United States Patent [19]

Kawai et al.

[11] Patent Number: 4,467,124
[45] Date of Patent: Aug. 21, 1984

[54] PREPARATION OF 1,1,1,3,3,3-HEXAFLUOROPROPANE-2-OL BY VAPOR PHASE CATALYTIC REACTION OF HEXAFLUOROACETONE HYDRATE WITH HYDROGEN

[75] Inventors: Toshikazu Kawai, Kamifukuoka; Akira Negishi, Sayama, both of Japan

[73] Assignee: Central Glass Company Limited, Ube, Japan

[21] Appl. No.: 493,658

[22] Filed: May 16, 1983

Related U.S. Application Data

[63] Continuation of Ser. No. 320,080, Nov. 10, 1981, abandoned.

[30] Foreign Application Priority Data

Nov. 11, 1980 [JP] Japan ................................ 55-157665

[51] Int. Cl.$^3$ .............................................. C07C 31/38
[52] U.S. Cl. .................................................. 568/842
[58] Field of Search ......................................... 568/842

[56] References Cited

U.S. PATENT DOCUMENTS 2,824,897  2/1958  Wujciak et al. .
3,418,337 12/1968  Middleton, Jr. .
3,468,964  9/1969  Swamer .
3,702,872 11/1972  Regan .
3,714,271  1/1973  Regan ................................. 568/842

FOREIGN PATENT DOCUMENTS 974612 11/1964  United Kingdom .

OTHER PUBLICATIONS

Gambaryan et al., Angewandte Chemie, Int. Ed. 5 (11), p. 947, (1966).

Primary Examiner—Howard T. Mars
Attorney, Agent, or Firm—Fleit, Jacobson, Cohn & Price

[57] ABSTRACT 1,1,1,3,3,3-hexafluoropropane-2-ol is obtained with high yield and high selectivity by vapor phase hydrogenolysis of a hydrate of hexafluoroacetone by using either a nickel catalyst or a palladium catalyst, or both. Hydrates of hexafluoroacetone are convenient to handling and storage because of being liquid or solid at room temperature and, moreover, can be refined to extremely high purity so that the catalyst exhibits long service life without suffering from poisoning. The hydrogenolysis reaction takes place at relatively low temperatures such as 40°–200° C. at atmospheric pressure.

13 Claims, No Drawings

PREPARATION OF 1,1,1,3,3,3-HEXAFLUOROPROPANE-2-OL BY VAPOR PHASE CATALYTIC REACTION OF HEXAFLUOROACETONE HYDRATE WITH HYDROGEN

This application is a continuation of application Ser. No. 320,080, filed Nov. 10, 1981 now abandoned.

BACKGROUND OF THE INVENTION

This invention relates to a process of preparing 1,1,1,3,3,3-hexafluoropropane-2-ol by vapor phase catalytic hydrogenolysis of hexafluoroacetone hydrate.

To our knowledge, 1,1,1,3,3,3-hexafluoropropane-2-ol is a compound useful as either a surface active agent or an emulsifying agent (according to Belgian Pat. No. 634,368), as a solvent for some polymers such as vinyl polymers of carboxylic acids (according to U.S. Pat. No. 3,153,004) and also as an intermediate of some anesthetic compounds (according to U.S. Pat. No. 3,346,448).

Usually 1,1,1,3,3,3-hexafluoropropane-2-ol is prepared from hexafluoroacetone, and various kinds of reduction of hydrogenation methods for this purpose have heretofore been proposed. Typical examples of such proposals are liquid phase reduction of hexafluoroacetone using sodium boron hydride as catalyst as represented by U.S.S.R Pat. No. 138,604, liquid phase hydrogenation of hexafluoroacetone using a platinum oxide catalyst as represented by U.S. Pat. No. 3,607,952, and vapor phase catalytic hydrogenation of hexafluoroacetone using a palladium catalyst which may be carried on carbon or alumina as represented by German Pat. No. 1,956,629.

Hexafluoroacetone as the starting material common among the above described known processes is a compound gaseous at room temperature. Accordingly in industrial practice of any of these processes care must be taken in storing, handling and transporting hexafluoroacetone. Moreover, it is very difficult and uneconomical to extremely purify gaseous hexafluoroacetone as an industrial material, and therefore it is inevitable that gaseous hexafluoroacetone for use in the aforementioned catalytic hydrogenation processes contains small or trace amounts of impurities such as hydrogen chloride, hydrogen fluoride and chloropentafluoroacetone. The presence of such impurities becomes a matter of serious disadvantage in industrial preparation of 1,1,1,3,3,3-hexafluoropropane-2-ol by any of the known catalytic hydrogenation processes because the impurities cause significant and rapid poisoning or deactivation of the catalyst.

SUMMARY OF THE INVENTION

It is an object of the present invention to provide an improved process of preparing 1,1,1,3,3,3-hexafluoropropane-2-ol, which process is vapor phase catalytic hydrogenolysis of hexafluoroacetone in principle but, nevertheless, is more convenient to industrial practice than the hitherto proposed processes and can be performed with very high yield and extremely high selectivity factor for 1,1,1,3,3,3-hexafluoropropane-2-ol without suffering from deactivation of the catalyst.

According to the invention, 1,1,1,3,3,3-hexafluoropropane-2-ol is prepared by making a hexafluoroacetone hydrate in vapor phase contact with hydrogen gas in the presence of either a nickel catalyst or a palladium catalyst, or both, such that the hexafluoroacetone hydrate undergoes hydrogenolysis.

We have reached this invention by first contemplating that hydrates of hexafluoroacetone, which can easily be obtained by contact of hexafluoroacetone with water, are either liquid or solid at room temperature and accordingly are convenient to handling, storage and transportation, then confirming that hexafluoroacetone in the form of a hydrate can be refined to very high purity far more easily than anhydrous and gaseous hexafluoroacetone, and finally discovering that vapor phase hydrogenolysis of a hexafluoroacetone hydrate to 1,1,1,3,3,3-hexafluoropropane-2-ol readily takes place and smoothly proceeds with very high yield and extremely high selectivity factor when either a nickel catalyst or a palladium catalyst, or both, is employed as the hydrogenolysis catalyst.

A hydrate of hexafluoroacetone is readily obtained by allowing hexafluoroacetone to be absorbed in water or to contact with water, and the degree of hydration can be controlled over a relatively wide range. Hydrates of hexafluoroacetone can be taken as to have a diol structure as expressed by a general formula $(CF_3)_2C(OH)_2 \cdot xH_2O$, wherein x is either zero or a positive number which is not necessarily an integer, and the monohydrate (x=0 in the above formula, m.p. is 49° C.) and the trihydrate (x=2, b.p. is 106° C.) are known as stable substances. These hydrates are readily soluble in water or uniformly miscible with water and are stable in the form of aqueous solution. Therefore, it will be permissible to regard an aqueous solution of a hydrate of hexafluoroacetone as another hydrate of hexafluoroacetone which, too, can be expressed by $(CF_3)_2(OH)_2 \cdot xH_2O$. In the present application, the term "hydrate of hexafluoroacetone" or "hexafluoroacetone hydrate" implies such an aqueous solution, too. Of course, dehydration of a hexafluoroacetone hydrate by using a known dehydrating agent such as sulfuric acid gives anhydrous hexafluoroacetone.

A catalytic hydrogenolysis reaction in a process according to the invention is represented by the following equation.

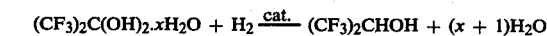

$$(CF_3)_2C(OH)_2 \cdot xH_2O + H_2 \xrightarrow{cat.} (CF_3)_2CHOH + (x+1)H_2O$$

That is, this process gives 1,1,1,3,3,3-hexafluororopane-2-ol in a state mixed with steam or water, but it is easy to recover high purity 1,1,1,3,3,3-hexafluoropropane-2-ol from this reaction product by a usual distillation procedure.

This reaction proceeds at the atmospheric pressure and at relatively low temperatures, and a short contact time suffices to complete the reaction.

The nickel catalyst is not required to be nickel alone and can be prepared in various forms and compositions as will later be described, and the same applies to the palladium catalyst, too.

The most important advantage of the process according to the invention is that the catalyst exhibits a remarkably long service life because it is possible to use a very highly refined hexafluoroacetone hydrate as the starting material and therefore it is possible to avoid poisoning of the catalyst by the influence of impurities contained in the starting material. From a practical point of view, it is also an important advantage of this process that the heat of reaction in this process is far smaller than that in the known processes for vapor phase catalytic hydrogenation of hexafluoroacetone, and therefore it becomes very easy to desirably control the reaction.

DESCRIPTION OF THE PREFERRED EMBODIMENTS

As mentioned hereinbefore, any hydrate of hexafluoroacetone or an aqueous solution of a hexafluoroacetone hydrate expressed by $(CF_3)_2C(OH)_2 \cdot xH_2O$, wherein x is zero or greater, can be used as the starting material in the process of the invention, though it is necessary to use it in a vaporized state. Besides, it is also possible to introduce anhydrous hexafluoroacetone into the reaction apparatus containing the catalyst together with steam such that hydration of hexafluoroacetone occurs within the reaction apparatus, though this is not particularly recommended.

It is suitable to choose the value of x in the above general formula within the range from 0 to 5.

As to the quantity of hydrogen gas used in the process of the invention, the minimum requirement is to be equivalent by mole to the hexafluoroacetone hydrate to be decomposed. However, there arises no problem by using excess quantity of hydrogen gas with the intention of utilizing it as carrier gas for the hexafluoroacetone hydrate.

A nickel catalyst for use in the present invention contains metallic nickel as its essential component. Preferably the metallic nickel is a reduced nickel obtained, for example, by reduction of a suitable nickel compound such as nickel carbonate, nickel oxide, nickel hydroxide or nickel sulfate in a hydrogen gas atmosphere or by thermal decomposition reduction of an organic nickel compound such as nickel formate, oxalate or acetate in a non-oxidizing atmosphere such as a carbon dioxide gas stream. Of course it is possible to use a catalyst substantially wholly consisting of metallic nickel. In practice, however, it is usual to use a catalyst in which metallic nickel is carried on a conventional carrier such as activated carbon or alumina or a catalyst in the form of granules or pellets in which metallic nickel is mixed with a supporting or bulking material such as clay, alumina, diatomite (kieselguhr), carbon or terra alba. If desired, at least one kind of auxiliary catalytic metal such as copper and/or chromium, or its oxide, may be added to the mixed nickel catalyst. For example, a nickel catalyst in the form of granules or pellets is produced by the steps of mixing a nickel salt such as nickel sulfate, metal oxide(s) such as alumina and/or chromium oxide and either diatomite or clay in an aqueous solution, adding an aqueous solution of sodium carbonate to the mixed solution to cause precipitation of nickel carbonate together with other compounds, filtrating and drying the obtained cake containing nickel carbonate, firing the dried cake to convert it into a mixed oxide, reducing the mixed oxide in a hydrogen gas atmosphere, and finally granulating or pelletizing the reduced material.

A palladium catalyst for use in the present invention contains metallic palladium as its essential component, usually carried on a familiar carrier material such as alumina or carbon. For example, a suitable catalyst is obtained by impregnating a carrier material with an aqueous solution of palladium dichloride, and heating the treating carrier material in hydrogen gas to thereby reduce palladium dichloride to palladium.

In the presence of either a nickel catalyst or a palladium catalyst the hydrogenolysis of a vaporized hexafluoroacetone hydrate represented by the above presented equation proceeds theoretically, and the catalyst is scarcely deactivated even when the reaction is performed continuously for a long period of time. If desired a nickel catalyst and a palladium catalyst may be used jointly. The minimum quantity of nickel and/or palladium in the catalyst allowable in the process of the invention is considered to be about 0.001% by weight of hexafluoroacetone in the hydrate to be decomposed, but in practice it is preferred that the nickel and/or palladium amounts to at least 0.005% by weight of hexafluoroacetone in the hydrate to be decomposed. There is no need of strictly specifying the maximum quantity of the catalyst because neither decomposition of 1,1,1,3,3,3-hexafluoropropane-2-ol formed by the intended catalytic reaction nor any side-reaction takes place even when an unnecessarily large quantity of catalyst is used.

From an industrial viewpoint, other kinds of hydrogenolysis catalysts are unsuitable to the process according to the invention. For example, when a platinum catalyst is used the rate of the hydrogenolysis reaction becomes very low, and when a ruthenium catalyst is used the catalyst is deactivated in a very short time.

The reaction temperature in the process of the invention must be above the boiling point of the hexafluoroacetone hydrate used as the starting material. If the reaction temperature is unduly high, there arises a possibility of further decomposition of the formed 1,1,1,3,3,3-hexafluoropropane-2-ol. Accordingly it is suitable that the reaction temperature falls within the range from 40° to 200° C., and more preferably within the range from 50° to 150° C. The hydrogenolysis reaction according to the invention proceeds smoothly and completely at atmospheric pressure, but there arises no problem even if the reaction is carried out at a somewhat elevated or reduced pressure.

In this hydrogenolysis reaction, usually a contact time of 2–3 seconds is sufficient to complete the reaction, but it is optional to prolong the contact time because it does not cause further decomposition of the formed 1,1,1,3,3,3-hexafluoropropane-2-ol insofar as the reaction temperature is maintained adequately as described above. In practice, the most suitable range of the contact time is from about 3 seconds to about 10 seconds.

The following examples are presented to further illustrate the invention. Needless to mention, these examples should not be taken as limitative of the invention. Some references are also presented for the sake of comparison.

EXAMPLE 1

The catalyst used in this example was a commercially available reduced nickel catalyst, which was in the form of pellets 5 mm in diameter and contained 45–47% of Ni, 2–3% of Cr, 2–3% of Cu, 27–29% of diatomite and 4–5% of graphite, all by weight. 20 g of this catalyst was packed in a Pyrex tube having an inner diameter of 13 mm and preliminarily activated by heating at about 180° C. in a stream of hydrogen gas passed through the tube and thereafter maintained at 110° C. Then, a mixed gas of a vaporized hexafluoroacetone hydrate expressed as $(CF_3)_2C(OH)_2 \cdot 4.5H_2O$ (30 g/hr as anhydrous hexafluoroacetone) and hydrogen (250 ml/min) was continuously passed through the packed column of the activated catalyst in the Pyrex tube to cause hydrogenolysis of the hexafluoroacetone hydrate by vapor phase catalytic reaction. The hydrogenolysis reaction proceeded rapidly so that the reaction temperature in the tube soon rose to 116°–118° C., and thereafter the reaction temperature remained at this level. The length of the catalyst column and the flow rate of the mixed gas were such that the contact time in this hydrogenolysis reaction was about 5 seconds. In the mixed gas, the mole ratio of hydrogen to the hexafluoroacetone hydrate was about 3.0:1.

At a stage after the lapse of one hour from the start of the introduction of the mixed gas into the reaction tube, it was confirmed that the conversion of the hexafluoroacetone hydrate was 99.2% and that the selectivity factor for 1,1,1,3,3,3-hexafluoropropane-2-ol was 100%. After continuation of the reaction for 20 hours, the conversion of the hexafluoroacetone hydrate was 98.9%, and the selectivity factor for 1,1,1,3,3,3-hexafluoropropane-2-ol was still 100%, meaning that the nickel catalyst in the reaction tube exhibited no loss of its activity during the time period of 20 hours.

EXAMPLE 2

Use was made of a commercially available palladium catalyst carried on alumina. This catalyst was in the form of pellets about 3 mm in diameter, and the content of Pd in the catalyst was 0.5% by weight. 20 g of this catalyst was packed in a Pyrex tube having an inner diameter of 13 mm and maintained in a hydrogen stream at a temperature of 120° C. Then, a mixed gas of a vaporized hexafluoroacetone hydrate expressed as $(CF_3)_2C(OH)_2.2.5H_2O$ (30 g/hr as anhydrous hexafluoroacetone) and hydrogen (400 ml/min) was continuously passed through the packed column of the catalyst in the Pyrex tube. The hydrogenolysis of the hexafluoroacetone hydrate proceeded rapidly with a slight rise in the temperature in the reaction tube, but soon the reaction temperature became stable and thereafter remained within the range from 125° to 130° C. In the mixed gas the mole ratio of hydrogen to the hexafluoroacetone hydrate was about 5.2:1, and the contact time in the reaction in this example was about 3 seconds.

After the lapse of one hour from the start of the introduction of the mixed gas into the reaction tube, the conversion of the hexafluoroacetone hydrate was 99.9% and the selectivity factor for 1,1,1,3,3,3-hexafluoropropane-2-ol was 100%. After continuation of the reaction for 20 hours, both the conversion value and the selectivity factor value were unchanged, meaning that the palladium catalyst in the reaction tube was not deactivated.

REFERENCE 1

Use was made of a commercially available ruthenium catalyst carried on carbon. This catalyst was in the form of granules passed through 4-mesh sieve (4.76 mm openings) and retained on 8-mesh sieve (2.38 mm openings), and the content of Ru in the catalyst was 0.5% by weight. 10 g of this catalyst was packed in a Pyrex tube having an inner diameter of 13 mm and maintained in a hydrogen gas stream at a temperature of 120° C. Then, a mixed gas of a vaporized hexafluoroacetone hydrate expressed as $(CF_3)_2(OH)_2.2.5H_2O$ (30 g/hr as anhydrous hexafluoroacetone) and hydrogen (250 ml/min) was continuously passed through the reaction tube. The hydrogenolysis reaction of the hexafluoroacetone hydrate proceeded rapidly so that the temperature in the reaction tube rose up to 130° C., but soon the reaction temperature became stable at a level slightly below 130° C. The mole ratio of hydrogen to the hexafluoroacetone hydrate in the mixed gas was about 3.0:1, and the contact time in the reaction in this experiment was about 5 seconds.

After the lapse of 20 minutes from the start of the introduction of the mixed gas into the reaction tube, the conversion of the hexafluoroacetone hydrate was 99.0% and the selectivity factor for 1,1,1,3,3,3-hexafluoropropane-2-ol was 100%. However, after continuation of the reaction for one hour the conversion value decreased to 20.2%, and after the lapse of additional one hour the conversion value was 0%. It is apparent that the ruthenium catalyst was deactivated very rapidly and seriously.

REFERENCE 2

In place of the palladium catalyst used in Example 2, 20 g of a commercially available platinum catalyst carried on alumina was packed in the Pyrex tube mentioned in Example 2 and maintained in a hydrogen gas stream at a temperature of 120° C. This catalyst was in the form of pellets about 3 mm in diameter and contained 0.5% by weight of Pt. Then the same mixed gas as the one used in Example 2 was continuously passed through the reaction tube at the same flow rate as in Example 2. In this case the reaction temperature remained within the range from 120° to 125° C., and the contact time was about 3 seconds.

After the lapse of one hour from the start of the reaction, it was confirmed that the conversion of the hexafluoroacetone hydrate was only 2.8%. That is, the expected hydrogenolysis reaction hardly proceeded because of unsuitableness of the platinum catalyst to this reaction.

EXAMPLE 3

In this example, 20 g of the nickel catalyst described in Example 1 was packed in the Pyrex tube and preliminarily activated in accordance with Example 1, and maintained at a temperature of 110° C. A hydrate of hexafluoroacetone was dissolved in a small quantity of water to obtain an aqueous solution that was expressed as $(CF_3)_2C(OH)_2.0.1H_2O$. This solution was vaporized and continuously introduced into the reaction tube (at a rate of 20 g/hr as anhydrous hexafluoroacetone) in a state mixed with hydrogen gas (170 ml/min). The hydrogenolysis reaction of the hexafluoroacetone hydrate proceeded rapidly, and soon the reaction temperature rose to 115°–117° C. and thereafter remained at this level. The mole ratio of hydrogen to the hexafluoroacetone hydrate in the mixed gas was about 3.0:1, and the contact time in this hydrogenolysis reaction was about 7 seconds.

At the stage after the lapse of one hour from the start of the introduction of the mixed gas into the reaction tube, it was confirmed that the conversion of the hexafluoroacetone hydrate was 100% and that the selectivity factor for 1,1,1,3,3,3-hexafluoropropane-2-ol was 100%. After continuation of the reaction for 48 hours, the conversion of the hexafluoroacetone hydrate was 99.9% and the selective factor for 1,1,1,3,3,3-hexafluoropropane-2-ol was still 100%. That is, the nickel catalyst in the reaction tube was not the least deactivated.

REFERENCE 3

In place of the nickel catalyst used in Example 3, 20 g of a commercially available ruthenium catalyst carried on alumina was packed in the Pyrex tube and maintained in a hydrogen gas stream at a temperature of 120° C. This catalyst was in the form of pellets about 3 mm in diameter and contained 0.5% by weight of Ru. Then, the same mixed gas of hydrogen and vaporized hexafluoroacetone hydrate solution as the one used in Example 3 was continuously introduced into the reaction tube at the same flow rate as in Example 3. The reaction temperature rose up to 135° C. in a short time but thereafter became stable at a level slightly below 135° C. The contact time in this reaction was about 7 seconds.

After the lapse of 20 minutes from the start of the introduction of the mixed gas into the reaction tube, the conversion of the hexafluoroacetone hydrate was 45.2%, and the selectivity factor for 1,1,1,3,3,3-hexafluoropropane-2-ol was 100%. However, after continuation of the reaction for one hour the conversion value was only 4.6%, indicating that the ruthenium catalyst in the reaction tube had been deactivated.

What is claimed is:

1. A process of preparing 1,1,1,3,3,3-hexafluoropropane-2-ol, comprising the step of making a hexafluoroacetone hydrate in vapor phase contact with hydrogen gas in the presence of at least one catalyst selected from the group consisting of a nickel catalyst and a palladium catalyst such that said hexafluoroacetone hydrate undergoes hydrogenolysis to 1,1,1,3,3,3-hexafluoropropane-2-ol, wherein said hexafluoroacetone hydrate is expressed by $(CF_3)_2C(OH)_2 \cdot xH_2O$, wherein x is $\geq 0.1$.

2. A process according to claim 1, wherein x is a number less than 5.

3. A process according to claim 1, wherein the hydrogenolysis reaction temperature is maintained in the range from 40° to 200° C.

4. A process according to claim 3, wherein the reaction temperature is maintained in the range from 50° to 150° C.

5. A process according to claim 3, wherein said hexafluoroacetone hydrate in vapor phase and hydrogen gas are continuously introduced into a reaction chamber in which said at least one catalyst is disposed.

6. A process according to claim 5, wherein said hexafluoroacetone hydrate in vapor phase, hydrogen gas and said at least one catalyst are allowed to contact with each other for a time period in the range from about 3 seconds to about 10 seconds.

7. A process according to claim 1, wherein said nickel catalyst contains a reduced nickel as an essential component thereof.

8. A process according to claim 7, wherein said nickel catalyst additionally contains a supporting material selected from the group consisting of clay, diatomite, terra alba, alumina and carbon and takes the form of pellets.

9. A process according to claim 7, wherein said nickel catalyst comprises a carrier which carries thereon said reduced nickel.

10. A process according to claim 9, wherein the material of said carrier is selected from the group consisting of alumina and carbon.

11. A process according to claim 1, wherein said palladium catalyst contains a reduced palladium as an essential component thereof.

12. A process according to claim 11, wherein said palladium catalyst comprises a carrier which carries thereon said reduced palladium.

13. A process according to claim 12, wherein the material of said carrier is selected from the group consisting of alumina and carbon.

* * * * *